United States Patent [19]

Leeder et al.

[11] Patent Number: 4,837,395
[45] Date of Patent: Jun. 6, 1989

[54] SINGLE STEP HETEROGENEOUS ASSAY

[75] Inventors: Sydney Leeder, Union City; Robert F. Zuk, Menlo Park, both of Calif.

[73] Assignee: Syntex (U.S.A.) Inc., Palo Alto, Calif.

[21] Appl. No.: 733,013

[22] Filed: May 10, 1985

[51] Int. Cl.$^4$ ............................................. G01N 33/53
[52] U.S. Cl. ......................................... 435/7; 435/14; 435/28; 435/184; 435/805; 436/810
[58] Field of Search ................... 435/7, 14, 28, 184, 435/805; 436/810

[56] References Cited

U.S. PATENT DOCUMENTS

| | | | |
|---|---|---|---|
| 3,413,197 | 11/1968 | Fraser | 435/28 |
| 3,862,885 | 1/1975 | Kano | 435/28 |
| 4,281,062 | 7/1981 | Kallis | 435/28 |
| 4,435,504 | 3/1984 | Zuk | 435/28 |
| 4,444,880 | 4/1984 | Tom | 436/530 |

FOREIGN PATENT DOCUMENTS 0058428 8/1982 European Pat. Off. .

OTHER PUBLICATIONS

White-Stevens I, Clinical Chemistry, 28(4), pp. 578-588 (1982).
White-Stevens II, Clinical Chemistry, 28(4), pp. 589-595 (1982).
"Cooxidation of the Clinical Reagent 3,5,3',5'-Tetramethylbenzidine by Prostaglandin Synthase", by Josephy et al., (Jul. 1982), in *Cancer Research*, 42:2567-2570.

*Primary Examiner*—Robert J. Warden
*Assistant Examiner*—Robert Benson
*Attorney, Agent, or Firm*—Theodore J. Leitereg

[57] ABSTRACT

Methods and compositions are provided for assays involving members of a specific binding pair ("sbp members") and members of a signal producing system ("sps members"). The signal producing system is capable of producing a detectible signal in relation to the presence or amount of an analyte in a sample suspected of containing the analyte. Exemplary of sps members are enzymes and enzyme substrates, which react with each other to produce a signal. The improvement of the present invention comprises temporarily delaying the production of the signal without subsequent reagent addition. The delay can be achieved by employing an inhibitor which can be an alternate substrate for the enzyme or a compound which reacts with the product of the enzyme and its substrate in an effective amount.

37 Claims, No Drawings

SINGLE STEP HETEROGENEOUS ASSAY

BACKGROUND OF THE INVENTION

1. Field of the Invention

A number of methods have been developed for the rapid and accurate determination of analytes, such as haptens, antigens and receptors. One group of assays involves a bibulous support and an enzyme conjugate. The presence or absence of a dye on the support is indicative of the amount of analyte in the assay medium. In developing these assays, it is desirable to simplify the protocol. Protocols which involve numerous independent manual steps may result in the introduction of numerous errors. Also, there can be greater variation in the results between different technicians. Furthermore, a multi-step protocol is usually tedious unless the protocol can be automated. Automated assays normally require sophisticated machines, which would preclude the use of the assay outside of large clinical laboratories.

It is therefore of interest to be able to simplify presently existing assays by simplifying protocols and maintaining the ease of conducting the assay or enhancing the result. It is particularly important that the assay reagents be provided in predetermined amounts and measurements by the user are avoided.

2. Description of the Prior Art

U.S. Pat. No. 4,168,146 describes a test strip immunoassay. U.S. Pat. No. 4,299,916 describes an enzyme assay employing a bibulous support and enzyme binding to the support in relation to the amount of analyte in an assay medium. See also U.S. Pat. No. 4,391,904, a continuation-in-part of U.S. Pat. No. 4,299,916. U.S. Pat. No. 4,366,241 involves an alternative device for performing immunoassays. application Ser. No. 398,505, filed July 15, 1982 now U.S. Pat. No. 4,435,504 describes an enzyme chromatographic immunoassay involving two enzymes.

A single step heterogeneous assay is disclosed in U.S. patent application Ser. No. 602,297, filed Apr. 20, 1984. An internally referenced test strip immunoassay for morphine is described by Litman et al. *Clin. Chem.* (1983) 29: 1598-1603.

SUMMARY OF THE INVENTION

Methods and compositions are provided for assays involving members of a specific binding pair ("sbp members") and members of a signal producing system ("sps members"). The signal producing system is capable of producing a detectible signal in relation to the presence or amount of an analyte in a sample suspected of containing the analyte. The improvement of the present invention comprises temporarily delaying the production of the signal without subsequent reagent addition. The sps members may comprise, for example, an enzyme and its substrate, which react with each other to produce a product that is capable of generating a signal either directly or by interaction with a dye or chromogen, for instance. The delay in production of signal can be achieved by employing an effective amount of a signal inhibitor, which can be an alternate substrate of the enzyme or which can react with the product of the enzyme and its substrate.

The invention has application to both heterogeneous and homogeneous assays when it is desirable to temporarily delay the production of a signal.

DESCRIPTION OF THE SPECIFIC EMBODIMENTS

As mentioned above, the present invention relates to assays involving sbp members and sps members where a signal is generated in relation to the amount of an analyte in a sample suspected of containing the analyte. As a result of the present invention, the production of the signal can be delayed without subsequent addition of a reagent. In a preferred embodiment, the reaction between at least two of the sps members is delayed.

Exemplary of such assays are enzyme immunoassays, both heterogeneous and homogeneous, For example, one such assay involes the binding of an enzyme to a bibulous support through the intermediacy of a reaction between homologous sbp members. The result of the assay is determined by a change in the development of color as a result of enzyme catalyzed product formation from a substrate. The enzyme substrate can be dissolved in the assay medium or impregnated in the support. An sbp member is generally non-diffusively bound to the bibulous support.

Another example of an assay to which the present invention can be applied is a protecton assay where an antibody to an enzyme restricts the activity of unbound enzyme but cannot restrict the activity of enzyme that is in an immume complex with the analyte. In such an assay, it is desirable to delay the signal until the enzyme activity is fully restricted. Such an assay is described in U.S. Pat. No. 4,233,401, the disclosure of which is incorporated herein by reference.

In the present invention, an inhibitor for the signal producing reaction is incorporated into the assay medium. The nature and amount of the inhibitor is such as to temporarily delay the production of the signal, i.e., to delay the production of the signal for, and only for, a finite time period. For instance, the production of signal can be delayed for a period of time equivalent to that required for the binding of the sbp member with its complementary sbp member. Alternatively, the production of signal can be delayed for a period of time equivalent to that required for the assay medium to traverse a strip of bibulous material.

Before proceeding further with the description of the specific embodiments of the present invention, a number of terms will be defined.

Analyte—the compound or composition to be measured, an sbp number which may be a ligand, which is mono- or poly valent, usually antigenic or haptenic, a single or plurality of compounds which share at least one common binding or determinant site, or a receptor.

The ligand analytes are characterized by being monovalent or polyvalent, while the receptor analytes may have a single or plurality of binding sites. The polyvalent analytes will normally be poly(amino acids), i.e., polypeptides and proteins, polysaccharides, nucleic acids, and combinations thereof. Such combinations or assemblages include bacteria, viruses, chromosomes, genes, mitochondria, nuclei, cell membranes and the like.

For the most part, the polyvalent ligand analytes will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight, and among hormones of interest, about 5,000 to 60,000 molecular weight.

An extensive listing of useful ligands may be found in U.S. Pat. No. 4,275,149, the disclosure bridging columns 12 to 17, which disclosure is incorporated herein by reference.

The monoepitopic ligand analytes will generally be from about 100 to 2,000 molecular weight, more usually from about 125 to 1,000 molecular weight. The analytes of interest include drugs, metabolites, pesticides, pollutants, and the like.

A large number of analytes of interest are listed in U.S. Pat. No. 4,275,149, columns 17 and 18, which disclosure is incorporated herein by reference.

For receptor analytes, the molecular weights will generally range from about $10^4$ to $2 \times 10^8$, more usually from about $3 \times 10^4$ to $2 \times 10^6$. For immunoglobulins, e.g., IgA, IgD, IgE, IgG and IgM, the molecular weights will generally vary from about 160,000 to about $10^6$. Enzymes will normally vary from about 10,000 to 600,000 daltons. Natural receptors vary widely, being generally at least about 25,000 molecular weight and may be $10^6$ and higher, including such materials as avidin, thyroxine binding globulin, thyroxine binding prealbumin, transcortin, membrane surface proteins, etc.

The polyepitopic ligand analytes will normally be poly(amion acids), i.e., polypeptides and proteins, polysaccharides, nucleic acids, and combinations thereof. Such combinations include bacteria, viruses, chromosomes, genes, mitochondria, nuclei, cell membranes and the like.

Member of a specific binding pair ("sbp member")—one of two different molecules, having an area on the surface or in a cavity which specifically binds to a particular spatial and polar organization of the other molecule. The members of the specific binding pair are referred to as ligand and receptor (antiligand). These will usually be members of an immunological pair, although other specific binding pairs such as biotin-avidin, hormones-hormone receptors, and the like are not immunological pairs. Complementary substances are ligand and receptor, while analogous substances are either ligands or receptors, which are differentiated in some manner, e.g., labeling.

Ligand—any organic compound for which a receptor naturally exists or can be prepared.

Receptor ("antiligand")—any compound or composition capable of recognizing a particular spatial and polar organization of a molecule, i.e., epitopic or determinant site. Illustrative receptors include naturally occurring receptors, e.g., thyroxine binding globulin, antibodies, enzymes, Fab fragments, lectins, nucleic acids, protein A, complement component Clq, and the like.

Ligand analog—a modified ligand which can compete with the analogous ligand for a receptor, the modification providing means to join a ligand analog to another molecule. The ligand analog will usually differ from the ligand by more than replacement of a hydrogen with a bond which links the ligand analog to hub or label, but need not.

Where a ligand is conjugated to another molecule or support, frequently the ligand will be modified to provide for a particular functional group at a particular site. This modification produces a product referred to as a ligand analog. U.S. Pat. No. 4,275,149 also has an extensive description of ligand analogs, bridging columns 18 and 19, which description is incorporated herein by reference.

Poly(ligand analog)—a plurality of ligands or ligand analogs covalently joined together, normally to a hub nucleus. The hub nucleus is a polyfunctional material, normally polymeric, usually having a plurality of functional groups, e.g., hydroxy, amino, mercapto, ethylenic, etc., as sites for linking. The hub nucleus is normally water soluble or at least dispersible and will usually be at least about 35,000 daltons, but generally not exceeding about 600,000 daltons. Illustrative hub nuclei include polysaccharides, polypeptides, including proteins, nucleic acids, ion exchange resins and the like.

Bibulous material—a porous material having pores of at least 0.182, susceptible to traversal by a mobile material such as a solvent, usually an aqueous medium, in response to capillary force. Such materials are generally hydrophilic or are capable of being rendered hydrophilic and include inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, etc.; either used by themselves or in conjunction with other materials; ceramic materials; and the like. The bibulous material can be attached to a support. On the other hand, the bibulous material may provide its own support. The bibulous material may be polyfunctional or be capable of being polyfunctionalized to permit convalent bonding of sbp members as well as to permit bonding of other compounds which form a part of the signal producing system.

The bibulous material can be coated with a wide variety of materials to provide for enhanced properties. Coatings may include protein coatings, polysaccharide coatings, sugars or the like, which are used particularly to enhance the stability of the materials conjugated to the support. These compounds can also be used for improved binding of the materials, such as the sbp member or sps member bound to the bibulous material.

The bibulous material can be activated with reactive functionalities to provide for covalent bonding of the organic materials to be conjugated to the strip such as those described in U.S. Pat. No. 4,168,146.

The amount of sbp member bound to the bibulous material will vary depending upon the amount required to bind all of the labeled sbp member and is decribed in U.S. Pat. No. 4,435,504. Binding of sbp members to the bibulous material may be accomplished by well-known techniques, commonly available in the literature. See, for example, "Immobilized Enzymes," Ichiro Chibata, Halsted Press, New York (1978) and Cuatrecasas, *J. Bio. Chem.* 245:3059 (1970).

The bibulous material can be a single structure such as a sheet cut into strips or it can be particulate material bound to a support or solid surface such as found, for example, in thin-layer chromatography.

The support for the bibulous material where a support is desired or necessary will normally be water insoluble, non-porous, and rigid and usually will be of the same length and width as the bibulous strip but may be longer or smaller. A wide variety of organic and inorganic materials, both natural and synthetic, and combinations thereof, may be employed provided only that the support does not interfere with the capillary action of the strip, or non-specifically bind assay components, or interfere with the signal producing system.

Illustrative polymers include polyethylene, polypropylene, poly(4-methylbutene), polystrene, polymethacrylate, poly(ethylene terephthalate), nylon, poly(vinly butyrate), glass, ceramics, metals, and the like.

Labeled-sbp member—a label, for example, a catalyst, usually an enzyme, conjugated to an sbp member, which is a member of the signal producing system.

Label—The label may be any molecule conjugated to another molecule or to the bibulous support and, where two molecules are involved, is arbitrarily chosen as to which molecule is the label. In the subject invention, the labels will be a member of the signal producing system that is conjugated to a support or an sbp member. The label will usually be a catalyst, e.g. coenzymes and enzymes.

Signal Producing System—The signal producing system may have one or more components, at least one component being the label conjugated to an sbp member. The signal producing system includes all of the reagents required to produce a measurable signal including the first sbp member when conjugated to a label and the components of the developer. When the first sbp member is not conjugated to a label, the label is normally bound to an sbp member complementary to the first sbp member and is usually included as part of the developer. Other components of the developer include substrates, coenzymes, enhancers, second enzymes, activators, cofactors, inhibitors, scavengers, metal ions, specific binding substance required for binding of signal generating substances, and the like. The components of the signal producing system may be bound to the strip such as coenzymes, substances that react with enzymic products, other enzymes and catalysts, and the like. The signal producing system provides a signal detectable by external means, normally by measurement of electromagnetic radiation, desirably by visual examination. For the most part, the signal producing system includes a chromophoric subtrate and enzyme, where chromophoric substrates are enzymatically converted to dyes which absorb light in the ultraviolet or visible region, phosphors or fluorophores.

The signal-producing system can include at least one catalyst, usually at least one enzyme, and at least one substrate and may include two or more catalysts and a plurality of substrates, and may include a combination of enzymes, where the substrate of one enzyme is the product of the other enzyme. The operation of the signal producing system is to produce a product which provides a detectable signal related to the amount of catalyst bound to the support, as a result of sbp member complex formation of the labeled sbp member.

The signal producing system provides for the production of a compound, which is normally the signal generating compound, but in some instances may react with another compound bound to the surface with the production, enhancement or destruction of the signal generating compound. While both enzymatic and non-enzymatic catalysts may be employed, usually there will be at least one enzyme catalyst employed in the signal producing system. In the event of there being only one catalyst, this catalyst will usually be conjugated to an sbp member through sbp member complex formation. In addition to the catalyst, there must be a substrate which undergoes a transformation which results in a change in a detectable signal at the measurement surface. For the most part, the product resulting from the transformation catalyzed by the labeled sbp member will be the signal generating compound.

Two catalysts may be employed, either a combination of an enzyme and a non-enzyme catalyst or two enzymes, where the two catalysts are related in that the product of one is the substrate of the other. In this system, there need be only one substrate which can undergo successive changes catalyzed by the catalysts, which results in the compound involved with production of a detectable signal. For the most part, however, there will normally be a substrate for the first enzyme in the series and a second compound, which serves as a precursor to the compound involved in the production of the signal, normally providing the compound which produces the signal. Thus, the product of the first enzyme may react with the precursor to the signal producing compound to provide the signal generating compound.

For the most part, the involved reactions will be hydrolysis or redox reactions. In the case of hydrolysis, a derivatized dye precursor that has an enzymatically labile bond and an enzyme that catalyzes its conversion to an insoluble dye product is illustrative of this type of system. In redox reactions, a first enzyme would produce an essential oxidizing substrate for the second enzyme, where the second enzyme catalyzes the reaction between the oxidizing substrate and a dye precursor.

Where two enzymes are used, the first enzymatic reaction may involve hydrolytic cleavage or a redox reaction of the substrate to provide a product which is the substrate of another enzyme. The first situation may be illustrated by glucose-6-phosphate being catalytically hydrolyzed by alkaline phosphatase to glucose, where glucose is a substrate for glucose oxidase. The second situation may be illustrated by glucose being oxidized by glucose oxidase to provide hydrogen peroxide which would enzymatically react with a leuco dye to produce a signal generator.

Coupled catalysts can also involve an enzyme with a non-enzymatic catalyst. The enzyme can produce a reactant which undergoes a reaction catalyzed by the non-enzymatic catalyst or the non-enzymatic catalyst may produce a substrate (includes coenzymes) for the enzyme. A wide variety of non-enzymatic catalysts which may be employed are found in U.S. Pat. No. 4,160,645, issued July 10, 1979, the appropriate portions of which are incorporated herein by reference.

Various combinations of enzymes may be employed to provide a signal generating compound. Particularly, combinations of hydrolases may be employed to produce an insoluble signal generator. Alternatively, combinations of hydrolases and oxidoreductases can provide the signal generating compound. Also, combinations of oxidoreductases may be used to produce an insoluble signal generating compound.

For combinations of enzymes one enzyme can be non-diffusively bound to the strip, while the other enzyme is conjugated to a sbp member. Additionally, one or more other members of the signal producing system can be bound to the strip depending on the particular signal producing system chosen or the particular protocol followed.

Because of the nature of the signal, in order to have a detectable signal, it is desirable to provide means for amplifying the signal produced by the presence of the label. Therefore, it will usually be preferable for the label to be a catalyst or luminescent compound, most preferably a catalyst. Preferable catalysts are enzymes and coenzymes, which can produce a multiplicity of signal generating molecules from a single label.

An enzyme or coenzyme is employed which provides the desired amplification by producing a product, which absorbs light, e.g., a dye, or emits light upon irradiation, e.g., a fluorescer. Alternatively, the catalytic reaction can lead to direct light emission, e.g., chemiluminescence. A large number of enzymes and coenzymes for providing such products are indicated in U.S. Pat. No. 4,275,149 bridging columns 19 to 23, and U.S. Pat. No. 4,318,980, columns 10 to 14, which disclosures are incorporated herein by reference.

Of particular interest is the use of a combination of enzymes, where the enzymes are related by the product of one enzyme being the substrate of the other enzyme. In this manner, stable precursors to labile substrates can be provided and the substrate for a second enzyme can be stored in combination with a first enzyme without a reaction being prematurely initiated.

A number of enzyme combinations are set forth in U.S. Pat. No. 4,275,149, bridging columns 23 to 28, which combinations can find use in the subject invention. This disclosure is incorporated herein by reference.

Of particular interest are enzymes which involve the production of hydrogen peroxide and the use of the hydrogen peroxide to oxidize a dye precursor to a dye. Particular combinations include saccharide oxidases, e.g., glucose and galactose oxidase, or heterocyclic oxidases, such as uricase and xanthine oxidase, coupled with an enzyme which employs the hydrogen peroxide to oxidize a dye precursor, i.g., a peroxidase such as horseradish peroxidase, lactoperoxidase, and microperoxidase. Additional enzyme combinations may be found in the subject matter incorporated by reference.

When a single enzyme is used as a label, other enzymes may find use such as hydrolases, transferases, and oxidoreductases perferably hydrolases such as alkaline phosphatase and $\beta$-galactosidase. Alternatively, luciferases may be used such as firefly luciferase and bacterial luciferase.

Illustrative coenzymes which find use include NAD[H]; NADP[H], pyridoxal phosphate; FAD[H]; FMN[H], etc., usually coenzymes involving cycling reactions, see particularly U.S. Pat. No. 4,318,980.

The product of the enzyme reaction will usually be a dye or fluorescer. A large number of illustrative fluorescers are indicated in U.S. Pat. No. 4,275,149, columns 30 and 31, which disclosure is incorporated herein by reference.

Ancillary Materials—Various ancillary materials will frequently be employed in the assay in accordance with the present invention. For example, buffers will normally be present in the assay medium, which can also include stabilizers. Frequently, in addition to these additives, additional proteins may be included, such as albumins, or surfactants, particularly non-ionic surfactants, e.g., polyalkylene glycols, or the like.

Immunochromatograph—The immunochromatograph has a sbp member, either ligand or receptor, bound in a region to a bibulous support which allows for the movement of a liquid by capillarity across the region with transport of the analyte and, as appropriate, any members of the signal producing system. The sbp member is non-diffusively bound to the support, either covalently or non-covalently. The area to which the sbp members is uniformly bound is referred to as the "immunosorbing zone." In addition, one or more members of the signal producing system can be non-diffusively bound to the bibulous support, either covalently or non-covalently. Furthermore, a reactant for an sps member such as an enzyme substrate can be bound to the support.

One device which is of particular interest is described in U.S. Pat. No. 4,168,146. This device, subject to modification, involves having an sbp member uniformly non-diffusively bound over a major portion of a bibulous strip. The end or tip of the device is immersed in a sample solution containing a complementary sbp (assay medium) and the sample solution is allowed to migrate upwards toward the other end of the device. After washing, the device is then immersed in a solution having an sbp member bound to an enzyme ("sbp member-enzyme conjugate"), which conjugate binds to remaining available sites on the device. The sites are available as a result of the presence or absence of the analyte in the sample. After washing the device, the device is then immersed in a developer solution having substrate for the enzyme. Location of detectable color on the device is related to the amount of analyte in the sample.

There have been numerous changes made in such a device, providing for simplified protocols. Of particular interest is the use of a combination of enzymes, where in addition to the sbp member pair, an enzyme is also bound over a major portion of the device. A second enzyme is bound to the sbp member. The two enzymes are related in that the substrate of one is the product of the other. By employing this combination of enzymes, one can simplify the protocol by combining the sbp member-enzyme conjugate with the substrate for the first enzyme and the sample. The result for the assay is determined by the farthest extent to which color develops, which may be predominantly a line or may extend over the entire area where the sbp member-enzyme conjugate is bound. For further description of this assay, see U.S. Pat. No. 4,435,504, the disclosure of which is incorporated herein by reference.

Immersion Strip—Another device of interest involves a bibulous member that is introduced into an assay sample. The bibulous member can be a small element mounted on a support and the element is completely immersed in the assay medium. Bound to the element will be an sbp member and, as appropriate, an enzyme, which serves the same function as described above. A sbp member-enzyme conjugate is employed which will bind to the element in proportion to the amount of analyte in the assay medium. The element can be removed from the assay medium, washed or not as the case may be and then immersed in a developer containing substrates for the enzyme. A colored insoluble product results where the analyte is present in the sample. The colored product is deposited upon the element in proportion to the amount of sbp member-(analyte)-enzyme conjugate bound to the element. This device is described in U.S. Pat. No. 4,391,904, the disclosure of which is incorporated herein by reference.

The immersion strip will often involve two elements, which are immersed in the assay medium. One element is an assay element and the other element is a standard.

Both the immunochromatograph and the immersion strip can be modified by impregnating into the bibulous element a substrate for the sbp member-enzyme conjugate which results in production of a color. Under the conditions of the assay, the substrate is available to the enzyme and is rapidly transformed by enzyme catalysis to a colored product which binds to the bibulous element to provide a detectable signal in relation to the amount of analyte in the assay medium. By impregnating the bibulous element with the substrate providing the color development, the reagent mixture which is employed for preparing the assay medium is simplified, background can be diminished, and a more quantitative result achieved. This improvement is described in U.S. patent application Ser. No. 602,297, filed Apr. 20, 1984, the disclosure of which is incorporated herein by reference.

Signal Inhibitor—Any compound which in the presence of the sps member temporarily delays the production of a detectible signal. The term "temporarily" means that signal production is delayed for, and only for, a finite period of time. The inhibitor can delay such reaction by interacting with the sps members such as by reacting with one of the sps members or by reacting with a product of the sps members. In this sense the signal inhibitor is exhaustible. For example, where an sps member is a catalyst, the signal inhibitor can be a compound that undergoes a reaction catalyzed by the catalyst. For sps members which are enzyme and enzyme substrate, the signal inhibitor can be an alternate substrate for the enzyme or a compound that reacts with the product produced by enzyme catalyzed reaction of the substrate.

A particular example of a signal inhibitor for an sps member which is a peroxidase enzyme is ascorbic acid or a derivative thereof such as a salt, an ester, or the like. Other examples of signal inhibitors in accordance with the present invention are ferricyanide, uric acid, hydroquinones, glutathione, dithiothreitol, sodium sulfite, and the like.

In carrying out the assay, the protocol will normally involve dissolving the sample suspected of containing the analyte in an aqueous medium. The sample may be derived from a wide variety of sources, such as physiologic fluids, illustrated by saliva, blood, serum, plasma, urine, ocular lens fluid, spinal fluid, etc., chemical processing streams, food, pesticides, pollutants, etc.

The aqueous medium can be up to about 40 weight percent of other polar solvents, particularly oxygenated solvents of from 1 to 6, more usually of from 1 to 4 carbon atoms, including alcohols, ethers and the like. Usually, the cosolvents will be present in less than about 20 weight percent.

The pH for the medium will usually be in the range of 4-11, more usually 5-10, and preferably in the range of about 6.5-9.5. The pH is chosen to maintain a significant level of binding affinity of the sbp members. Various buffers may be used to achieve the desired pH and maintain the pH during the assay. Illustrative buffers include borate, phosphate, carbonate, tris, barbital and the like. The particular buffer employed is not critical, but in individual assays, one buffer may be preferred over another.

Desirably, from about 0.05 to 0.5 wt. % of a non-ionic detergent is included with the sample. Various polyoxyalkylene compounds may be employed of from about 200 to 20,000 daltons.

Moderate, and desirably substantially constant, temperatures are normally employed for carrying out the assay. The temperatures for the assay and production of a detectable signal will generally be in the range of about 10°-50° C., more usually in the range of about 15°-50° C., and frequently will be ambient temperatures, that is, about 15°-25° C.

The concentration, in the liquid sample, of analyte which may be assayed will generally vary from about $10^{-4}$ to about $10^{-15}$M, more usually from about $10^{-6}$ to $10^{-14}$M. Considerations, such as the concentration of the analyte of interest and the protocol will normally determine the concentration of the other reagents.

While the concentrations of many of the various reagents in the sample and reagent solutions will generally be determined by the concentration range of interest of the analyte, the final concentration of each of the reagents will normally be determined empirically to optimize the sensitivity of the assay over the range of interest. However, with certain protocols, individual reagents may be used in substantial excess without detrimentally affecting the sensitivity of the assay.

Other reagents which are members of the signal producing system can vary widely in concentration depending upon the particular protocol and their role in signal production. Usually the labeled sbp member will not exceed 10 times the maximum concentration of interest of the analyte and will not be less than about 0.5 times the minimum concentration of interest. In most other situations, the amount of the other reagents involved in sbp member complex information may be present in an amount substantially less than the binding equivalent of analyte or in substantial excess to the binding equivalent of analyte. Therefore, no simple relationship can be provided.

The signal inhibitor will be present in the assay medium in an effective amount, that is, an amount sufficient to temporarily delay the production of the signal. Therefore, this amount will be determined according to the length of time one desires to achieve such delay, the nature of the sps members, the nature of the signal inhibitor, whether the assay in heterogeneous or homogeneous and the like. For the most part the signal inhibitor will be present in the assay medium in an amount of about $10^{-7}$ to $5 \times 10^{-1}$ molar, preferably, $10^{-6}$ to $10^{-2}$ molar, and more preferably, $10^{-5}$ to $10^{-3}$ molar.

In carrying out the assay, the protocol will normally involve dissolving the sample into the assay medium which also can contain one or more sps members and an effective amount of the signal inhibitor.

For the immunochromatograph, one end of the chromatograph will be contacted with the assay medium. Sufficient time will be allowed for the solvent front to completely traverse the immunosorbing zone. The zone has a sufficient amount of an sbp member bound thereto to insure that all of the analyte becomes bound in the zone without exhausting the sbp member bound in the zone.

While various protocols may be employed, for the most part, the assay solution will involve the sample, the analyte, the sbp member-conjugate, and the signal inhibitor, as well as any additional reagents, such as buffer, detergents, additional substrates with the enzyme, etc. The particular concentration of the various agents which provides a useful result can be determined empirically.

The assay medium will be allowed to traverse the immunosorbing zone for the sufficient time, so that the solvent front has traversed all or substantially all of the immunosorbing zone. The resulting immunochromatograph will then be allowed to stand for sufficient time for the signal inhibitor to be exhausted and for color to develop. The height of the color may be read as indicative of the amount of analyte in the assay medium.

For the immersion strip, the strip will be immersed in the assay medium, which will have similar components to that indicated above, having at least the enzyme conjugate, the sample, and the signal inhibitor. After sufficient time for the reaction of the enzyme conjugate with its reciprocal binding member bound to the bibulous element and for exhaustion of the signal inhibitor, the element may be removed from the assay medium and either read directly if the signal inhibitor is exhausted or held for sufficient time for detectible signal to be observed. Washing may or may not be necessary.

For a protection assay involving an antibody to an enzyme which restricts enzyme activity of the non-complexed enzyme, the assay medium will include the sample suspected of containing the analyte, a conjugate of an analog and an enzyme, antibody to the analyte, antibody to the enzyme, an enzyme substrate, and a signal inhibitor in an amount sufficient to delay production of the signal until the enzyme activity is fully restricted. After an amount of time has past for the enzyme activity to be restricted and for the signal inhibitor to be exhausted, the enzymatic activity of the medium is determined and related to a standard to determine the amount of analyte.

As a matter of convenience, the reagents can be provided in a kit in packaged combination in predetermined amounts for use in assaying for an analyte. The reagents will include an enzyme or enzymes, including an enzyme labeled sbp member, substrate for the enzyme or enzymes, a signal inhibitor, any additional substrates and cofactors required by the enzyme, the dye precursor, which provides the detectable chromophore or fluorophore, and, where appropriate bibulous strips or the like. In addition, other additives such as ancillary reagents may be included, for example, stabilizers, buffers, and the like. The relative amounts of the various reagents may be varied widely, to provide for concentrations in solution of the reagents which substantially optimize the sensitivity of the assay. The reagents can be provided as dry powders, usually lyophilized, including excipients, which on dissolution will provide for a reagent solution having the appropriate concentrations for performing the assay.

EXAMPLES

The following examples are offered by way of illustration and not by way of limitation.

The following abbreviations are used hereafter: h- hour, HRP— horse radish peroxidase; NHS— N-hydroxy succinimide; EDCA— ethyl dimethylamino-propyl carbodiimide; DMF— dimethyl formamide; BSA— bovine serum albumin. Temperatures not otherwise indicated are Celsius, while parts are by weight except for mixtures of liquids which are by volume.

Example 1

Preparation of HRP-Oxyamine

To 5 ml of 10 mg/ml horse radish peroxidase in 5 mM sodium acetate, pH 4.5 buffer, was added 50 ml 0.2M sodium periodate and the mixture stirred for 30 min, followed by chromatography on a G-50 Sephadex column, eluting with 2 mM sodium acetate buffer, pH 4.5. The protein fractions were pooled to 29 ml, the mixture cooled to 4° C. and 2.9 ml of 0.2M 2,2'-oxy-bis-ethylamine in 0.5M carbonate buffer, pH 9.5 at 40° C. added. The pH of the mixture was ajusted to 9.5 with 1N sodium hydroxide, stirred for 2 h and 3.52 ml of a 4 mg/ml sodium borohydride-water solution added and the mixture allowed to react for 3 h, followed by chromatography through a Sephadex® G-50 column.

The above procedure was repeated using 400mg of HRP and 3.5 g of 2,2'-oxy-bis-ethylamine. No significant change in enzyme activity was observed between the native amine and the modified amine, which has about four additional amino groups.

EXAMPLE 2

Preparation of Glucose Oxidase Amine

Glucose oxidase (Sigma, E.C. 1.1.3.4) was concentrated from 360 ml to 60 ml (32 mg/ml) and dialyzed twice, and filtered. To 51.5 ml of glucose oxidase solution was added dropwise 5.15 ml of 0.2M sodium periodate, the reaction occurring over 25 minutes. The product was chromatographed on a 2.5×60 cm column of Sephadex G-50 using 2 mM sodium acetate pH 4.5, and the major glucose oxidase peaks pooled to yield 91.5 ml of a solution containing the aldehyde derivative. To the solution was added dropwisw 6 ml of 3 M ethylene diamine in 0.2 M sodium carbonate, pH 9.5, and the reaction allowed to proceed for 3 hours. To the mixture was added about 3.9 ml of 10 mg/ml sodium borohydride. The mixture was incubated overnight and then chromatographed to remove the sodium borohydride.

EXAMPLE 3

Preparation of Immunochromatograph

A sheet (185×230 mm) of Whatman 31ET paper was immersed in 1.8 l. pryridine, 0.2M in carbonyl-diimidazole and the mixture was gently stirred for one hour at room temperature. Additional sheets were activated in the same activating solution. Each sheet was then washed with 300 ml tetrahydrofuran and air dried with an air gun over about 20 sec.

A solution (100 ml) containing antitheophylline (2 mg/ml) and glucose oxidase amine (0.1 mg/ml) in bicarbonate buffer, pH 9.5 (70 mM $NaHCO_3$ and 30 mM $Na_2CO_3$) was placed in a tray. A sheet of paper prepared as above was placed in the tray and was dipped into with the above antibody solution. After 1 h, 500 ml of ethanolamine was added to the tray. After an additional hour the sheet was removed from the tray and washed 2 times with 500 ml of a buffer containing 100 mM $NaH_2PO_4$, pH 7.0, and 200 mM NaCl. The sheet was then washed 1 time with 500 of deionized water.

Following the above washings the sheet was soaked for about 20 min. in either 250 ml of aqueous 0.5% polyvinylalcohol, or if enzyme substrate was to be impregnated on the immunochromatograph, 250 ml of aqueous 0.5% polyvinyl alcohol with 400 μg/ml 4-chloro-1 naphthol. The sheet was removed from the polyvinylalcohol solution and was blotted and tunnel-dried for 5 min. at 65° C.

EXAMPLE 4

Conjugation of Theophylline and HRP

Into a reaction flask was introduced 8.1 mg of 1methyl-3-(3'-carboxypropyl)xanthine, 3.8 mg of NHS, 6.7 mg EDAC and 125 μl DMF and the mixture allowed to stand overnight at room temperature.

To four-1.3 ml samples of HRP-oxyamine (1mg) in 0.1M sodium carbonate, pH 9.0, was added varying amounts of the ester prepared above to provide for preparations having mole ratios of theophylline to HRP of 400, 200, and two of 100 each. Into the first reaction mixture (400 mole ratio) was added 0.217 µl ml of DMF and 66 µl of the above ester in 8.25 µl increments over a period of about 2 h. Into the second reaction mixture (200 mole ratio), 0.238 ml of DMF was added and 33 µl of the ester added incrementally in 8.25 µl increments. Into the third reaction mixture (100 mole ratio), 0.24 ml of DMF was added and 16.5 µl of the ester added in 8.2 µl increments, while in the final reaction mixture (100 mole ratio), no DMF was added, and 8.25 µl of the ester was added in 2.1 µl increments. During the addition, the temperature was maintained at 4°, and the mixture then allowed to stand overnight at 4°.

The reaction mixtures were then worked up by chromatography on G-25 Sephadex ® with standard buffer. Folin and UV spectroscopic analysis indicated theophylline/HRP ratios of 6.9, 4.0, 1.6 and 2.1, respectively.

EXAMPLE 5

Immunochromatographic Assay

Theophylline (10 µl each) was combined with a buffered medium such that the concentration therein was 0,10 and 40 µg/ml of theophylline, respectively. The buffered medium was an aqueous buffered medium (pH 7.0 phosphate buffered saline) which further contained 150ng/ml of the conjugate of Example 4, 0.05M glucose, 1 mg/ml of BSA, and 200 µg/ml of 4-chloro-1-naphthol. Each sample was made 0.001M, 0.002M, 0.01M, and 0.02M respectively, in ascorbic acid. A control contained no ascorbic acid but did contain the other reagents enumerated above.

The 4 chloro-l-naphthol impregnated sheet prepared in Example 3 was previously cut into strips 6.5×90mm. The end of a strip (about 5 mm) was dipped into each of the above samples and the medium was allowed to traverse the strips for a period of 10 minutes.

The strips were observed for color development. On the strips contacted with the assay medium containing ascorbic acid, color development was delayed for approximately 3 min. (0.001M), 7 min. (0.002M), 30 min. (0.01M, and 60 min. (0.02M), respectively. Color developed in the upper portion of the immunosorbing zone first and gradully spread downward to the bottom of the strip. The color front delineation was sharp and color formation was even. The results were superior to the Control wherein color development began immediately from the bottom upward and gave a diffuse front an uneven color.

EXAMPLE 6

Immunchromatographic Assay of Whole Blood Samples Employing 4-Chloro-1-Naphthol as a Chromogen Whole blood samples (12.5µl) containing zero, 2.5, 5, 10, 20, and 40 µg/ml of theophylline, respectively, were combined with 1.0 of buffered medium. The buffer medium was an aqueous medium (pH 7.0 phosphate buffered saline) which further contained 1.6 µg/ml of the conjugate of Example 4, 0.05M glucose, 0.003M ascorbate, 400 µg/ml 4-chloro-1-naphthol, 16 mg/ml BSA, and 15 µl of antibody to human red blood cells.

Sheets prepared in Example 3 were previously cut into 4.5×90 mm strips. The end of the strip (about 5 mm) was dipped one each into the above samples and the medium allowed to traverse by capillary action to the top of the strip (10 mintues).

The strips were observed for color development after 15 minutes. The distance from the bottom of the strip to the top of the color zone was measured for the samples with differing theophylline concentration to provide the following results.

| Theophylline (µg/ml) | Color Zone Distance (mm) |
| --- | --- |
| Zero | 22 |
| 2.5 | 32 |
| 5 | 37 |
| 10 | 44.5 |
| 20 | 55.5 |
| 40 | 66 |

EXAMPLE 7

Immunochromatographic Assay Employing Di-Carboxidine as a Chromogen

Whole blood samples (12.5 µl) containing 5, 15, and 30µg/ml of theophylline, respectively, was combine with 1.0 ml of buffered medium. The buffer medium was an aqueous medium (pH 7.0 phosphate buffered saline) which further contained 1.0 µg/ml of the conjugate of Example 4, 2 mg/ml BSA, 600 µg/ml dicarboxydine, 0.002 M ascorbate, and 40 µg/ml antibody to human red blood cells.

Sheets prepared in Example 3 (without impregnated enzyme substrate) were previously cut into strips 4.5×90 mm. The end of the strip (about 5 mm) was dipped one each into the above samples and the medium allowed to traverse by capillary action to the top of the strip (10 minutes).

The strip were observed for color development after 15 minutes. The following results were obtained with different theophylline samples by measuring the distance from the bottom of the strip to the top of the color zone.

| Theophylline (µg/ml) | Distance of Color Zone from Bottom of the Strip*, (mm) |
| --- | --- |
| 5 | 32.6 |
| 15 | 46.7 |
| 30 | 57.5 |

*Mean of the ten values

The above results demonstrate that an accurate assay for theophylline can be carried out on whole blood samples in accordance with the present invention in a single step. Color development is sharper, more even, and superior to an assay medium which did not contain a signal inhibitor, in the above Examples, ascorbid acid.

Although the foregoing invention has been described in some detail by way of illustration and example for the purposes of clarity and understanding, it will be obvious that certain changes or modifications may be practiced within the scope of the appended claims.

What is claimed is:

1. In an assay method involving in an aqueous medium the reaction of members of a specific binding pair ("sbp members") and the reaction of members of a signal producing system ("sps members") capable of producing a detectable signal in relation to the presence or amount of an analyte in a sample suspected of containing said analyte wherein at least one sbp member is bound to at least one sps member, the improvement which comprises temporarily delaying the production of said signal by employing an effective amount of a signal inhibitor present in said aqueous medium prior to the production of said signal, said signal inhibitor being a compound that chemically inhibits the reaction of an sps member.

2. The method of claim 1 wherein the production of said signal is delayed by delaying the reaction of a least two of said members.

3. The method of claim 1 wherein said sps members are enzyme and substrate for said enzyme.

4. The method of claim 3 wherein said enzyme is a peroxidase.

5. The method of claim 3 wherein said inhibitor is an alternative substrate for said enzyme.

6. The method of claim 3 wherein said inhibitor reacts with a product of the reaction of said enzyme with its substrate.

7. The method of claim 5 wherein said inhibitor is ascorbic acid or salt or ester thereof.

8. A method for determining the presence of an analyte in a sample suspected of containing said analyte wherein said analyte is a member of a specific binding pair ("sbp member") consisting of ligand and its complementary receptor and wherein an aqueous medium containing said sample traverses bibulous material, which method comprises
   (a) contacting said medium with said bibulous material to which an sbp member is non-diffusively bound, said medium further containing (1) a conjugate of an sbp member and an enzyme, wherein said enzyme is part of a signal producing system including an enzyme substrate and (2) an amount of an exhaustible inhibitor of the signal producing reaction sufficient to chemically delay the production of said signal for a period of time at least equivalent to the period of time for said medium to substantially traverse said bibulous material,
   (b) allowing said medium to traverse said bibulous material, and
   (c) examining said bibulous material for a detectable signal related to the amount of said analyte in said sample.

9. The method of claim 8 wherein said exhaustible inhibitor delays the production of said signal by delaying the reaction of enzyme and enzyme substrate.

10. The method of claim 8 wherein said ligand is an analyte.

11. The method of claim 8 wherein said ligand is theophylline.

12. The method of claim 8 wherein said complementary receptor is an antibody.

13. The method of claim 8 wherein said complementary receptor is an antibody specific for theophylline.

14. The method of claim 8 wherein said inhibitor is an alternate substrate for said enzyme.

15. The method of claim 8 wherein said inhibitor reacts with a product of the reaction of said enzyme and said substrate.

16. The method of claim 8 wherein said inhibitor is ascorbic acid or a salt or ester thereof.

17. The method of claim 11 wherein said aqueous medium contains a first enzyme bound to and sbp member and said bibulous material contains a second enzyme wherein the enzymes are related in that the product of one enzyme is the substrate for the other enzyme.

18. The method of claim 17 wherein said first enzyme is horse radish peroxidase and said second enzyme is glucose oxidase.

19. A composition for use in an assay involving members of a specific binding pair ("sbp members") and members of a signal producing system ("sps members") and at least one sbp member is bound to an sps member, said composition comprising
   in an aqueous medium (1) one or more of said sps members wherein said signal producing system is capable of producing a detectible signal in relation to the presence or amount of an analyte in a sample suspected of containing said analyte and wherein at least one sbp member is bound to a bibulous support and (2) an inhibitor for the signal producing reaction in an amount of $10^{-5}$ to $10^{-3}$M to temporarily delay the production of said detectible signal, said inhibitor being a compound that chemically inhibits the reaction of an sps member.

20. The composition of claim 19 wherein said sps members comprise an enzyme and substrate for said enzyme.

21. The composition of claim 20 wherein said enzyme is a peroxidase.

22. The composition of claim 20 wherein said inhibitor is an alternate substrate for said enzyme.

23. The comopsition of claim 20 wherein said inhibitor reacts with a product of the reaction of said enzyme and said substrate.

24. The composition of claim 23 wherein said inhibitor is ascorbic acid or a salt or ester thereof.

25. A composition for use in a chromatographic assay wherein an aqueous medium containing a conjugate of a member of a specific binding pair ("sbp members") and an enzyme traverses bibulous material having the reciprocal sbp member bound thereto, said enzyme being part of a signal producing system which includes one or more enzymes, said system being capable of producing a detectible signal relative to the amount of an analyte in a sample suspected of containing said analyte, which composition comprises -
   (a) said conjugate,
   (b) substrate for said enzyme, (c) an exhaustible inhibitor for the signal producing reaction in an amount sufficient to delay chemically the signal producing reaction for a period of time at least equivalent to the period of time for said medium to substantially traverse said bibulous material, said amount being such that a said composition in an aqueous medium contains $10^{-5}$ to $10^{-3}$M of said inhibitor.

26. The composition of claim 25 which further comprises a compound reactive with the product of said enzyme and said enzyme substrate to produce a detectable signal.

27. The composition of claim 26 wherein said compound is a chromogen.

28. The composition of claim 25 wherein said sbp member in said conjugate is an analog of said analyte.

29. The composition of claim 25 wherein said sbp member in said conjugatge is an analog of theophylline.

30. The composition of claim 25 wherein said reciprocal sbp member is an antibody.

31. The composition of claim 25 wherein said reciprocal sbp member is an antibody specific for theophylline.

32. The composition of claim 25 wherein said inhibitor is an alternative substrate for said enzyme.

33. The composition of claim 25 wherein said inhibitor reacts with a product of the reaction of said enzyme and said substrate.

34. The composition of claim 25 wherein said inhibitor is ascorbic acid or a salt or ester thereof.

35. The composition of claim 25 wherein said aqueous medium contains a conjugate of a first enzyme and an sbp member and said bibulous material contains a second enzyme bound thereto wherein the enzymes are related in that the product of one enzyme is the substrate for the other enzyme.

36. The composition of claim 35 wherein said first enzyme is horse radish peroxidase and wherein said second enzyme is glucose oxidase.

37. A kit for use in an assay method involving the reaction of members of a specific binding pair ("sbp members") and members of a signal producing system ("sps members") capable of producing a detectible signal in relation to the presence or amount of an analyte in a sample suspected of containing said analyte, which kit comprises in packaged form the composition of claim 19.

* * * * *